United States Patent
Hunt et al.

(10) Patent No.: US 9,404,854 B2
(45) Date of Patent: Aug. 2, 2016

(54) SECOND AND THIRD ORDER SIMULTANEOUSLY NON-LINEAR OPTICAL PROCESSES AND MEASUREMENTS FOR SURFACE ANALYSIS

(71) Applicant: The Boeing Company, Huntington Beach, CA (US)

(72) Inventors: Jeffrey H. Hunt, Thousand Oaks, CA (US); John H. Belk, St. Louis, MO (US)

(73) Assignee: The Boeing Company, Chicago, IL (US)

(*) Notice: Subject to any disclaimer, the term of this patent is extended or adjusted under 35 U.S.C. 154(b) by 0 days.

(21) Appl. No.: 14/520,850

(22) Filed: Oct. 22, 2014

(65) Prior Publication Data

US 2016/0116401 A1    Apr. 28, 2016

(51) Int. Cl.
| | | |
|---|---|---|
| *G01J 5/02* | (2006.01) | |
| *G01N 21/3581* | (2014.01) | |
| *G01N 21/65* | (2006.01) | |

(52) U.S. Cl.
CPC ............ *G01N 21/3581* (2013.01); *G01N 21/65* (2013.01); *G01N 2021/653* (2013.01); *G01N 2201/06113* (2013.01)

(58) Field of Classification Search
CPC .................. G01N 17/006; G01N 21/3581
See application file for complete search history.

(56) References Cited

U.S. PATENT DOCUMENTS

| | | |
|---|---|---|
| 7,304,305 B2 | 12/2007 | Hunt |
| 8,736,838 B2 | 5/2014 | Herzinger |
| 8,743,368 B2 | 6/2014 | Meyers et al. |
| 2013/0161541 A1* | 6/2013 | Kim ............ G02F 2/002 250/504 R |

OTHER PUBLICATIONS

Stoik et al., "Nondestructive evaluation of aircraft composites using reflective terahertz time domain spectroscopy," 2010, NDT&E International, vol. 43, pp. 106-115.*
Anastasi et al., "Terahertz NDE for Under Paint Corrosion Detection and Evaluation," The 4th International Workshop on Ultrasonic and Advanced Methods for Nondestructive Testing and Material Characterization, Jun. 19, 2006 at UMass Dartmouth, N. Dartmouth, MA—published in www.ndt.net.*
Andreev et al., "Probing of surface and bulk optical nonlinearities using surface plasmon optics," 2004, OSA/CLEO 2004, 3 pages.*
Oda, "Uncooled Bolometer-type Terahertz Focal Plane Array and Camera for Real-Time Imaging," C.R. Physique, vol. 11, 2010, pp. 496-509.

* cited by examiner

*Primary Examiner* — Kiho Kim
(74) *Attorney, Agent, or Firm* — Nexsen Pruet, PLLC (57) ABSTRACT

Methods, systems and apparatuses are disclosed for interrogating characteristics of a substrate material surface and subsurface by evaluating Terahertz output signals generated by non-Terahertz, optical source inputs.

24 Claims, 5 Drawing Sheets

SECOND AND THIRD ORDER SIMULTANEOUSLY NON-LINEAR OPTICAL PROCESSES AND MEASUREMENTS FOR SURFACE ANALYSIS

TECHNOLOGICAL FIELD

The present disclosure relates to monitoring material surfaces. More particularly the present disclosure relates to monitoring material surfaces using second and third order non-linear optics to evaluate and characterize a substrate material surface and subsurface.

BACKGROUND

Surface characterization of materials is an important aspect of determining a material's condition and must be monitored to determine, material failure, fatigue, etc. However known surface diagnostic methods that are non-invasive (not requiring alteration or destruction of the material, or even physical removal from a structure) have not been satisfactory or useful in a scalable setting. This is because signals generated by known techniques mare not surface sensitive to the degree required. As a result surface modifications such as cracking, corrosion, stress, fatigue, etc. are very difficult to detect.

In non-linear optical, or wave mixing processes, outputs are produced at sum, difference or harmonic frequencies of the input(s). Second order non-linear optics, or three wave mixing involves combining two inputs to produce one output at one of the combined frequencies. The use of second order non-linear optical surface spectroscopy to examine physical properties of a material surface is known. However, practical constraints on such known methods have impeded progress on the material evaluation and characterization below the surface of a material under inspection.

The terahertz (THz) range refers to electromagnetic waves with frequencies between 100 GHz and 10 THz, or wavelengths between 3 mm and 30 µm, existing in the radiation spectrum between the microwave and infrared region. Terahertz waves are known to pass through a variety of amorphous and opaque substances. In addition, many biomolecules, proteins, explosives or narcotics also feature characteristic absorption lines, so-called spectral "fingerprints", at frequencies between 0.3 and 3 THz. The two main advantages of THz radiation are thus the penetration of conventionally opaque materials on one hand, and a high chemical selectivity on the other hand. Terahertz imaging is therefore thought to be a non-destructive technique for interrogating dielectric (non-conducting) materials. The use of THz waves for non-destructive evaluation of materials enables inspection of multi-layered structures and can therefore identify abnormalities from foreign material inclusions (contamination) delamination, heat damage, etc.

The spectroscopic frequency band of a 0.5 to 3 THz is not easily accessible. Electronic sources like Gunn or Schottky diodes with subsequent frequency multipliers, provide high output levels (mW range) up to some 100 GHz, yet become inefficient in the sub-millimeter range. Direct optical sources, like quantum cascade lasers, are usually limited to frequencies greater than 5 THz, even when operated at cryogenic temperatures.

Optoelectronic terahertz generation is an expression for indirect methods, where near-infrared laser light illuminates a metal-semiconductor-metal structure, generating a photocurrent that becomes the source of a terahertz wave. Both pulsed and continuous-wave (cw) techniques have been realized, and both have their advantages and limitations. Pulsed terahertz radiation offers a higher bandwidth (typically from about 0.1 to about 5 THz) and permits very fast measurements—a spectrum can be acquired within milliseconds. On the other hand, the frequency resolution is limited to several GHz. Vice versa, a cw system features a somewhat lower bandwidth (typically from about 0.1 to about 2 THz) and requires longer measurement times (acquiring a spectrum takes several minutes), yet the frequency can be controlled with extreme precision (down to single MHz).

Composite materials such as fiberglass, Kevlar and carbon fiber are increasingly being used as structural components in aircraft because of their high strength to weight ratios, improved performance, reduced corrosion, etc. compared with other known structural materials. However, composites can be weakened by various defects and stress during their life cycle. Further, routine maintenance of composites requires complicated inspection and repair techniques.

Terahertz radiation offers a non-invasive, non-contract, non-ionizing method of assessing composite part condition. However, THz sources have generally been difficult to produce. While there has been recent development using quantum cascade lasers, such devices remain largely in the developmental stage, and are intrinsically low-power devices. This limits their application to selected industrial manufacturing environments that require ease of operation and speed of data acquisition. In addition, use of THz surface of a substrate surface using presently available technology would still lack the degree of surface specificity required for interrogating composite and other opaque surfaces.

The use of composite materials in modern manufacturing scenarios requires the existence of diagnostics that can reliably interrogate surface and subsurface composite characteristics. Such interrogation developments were not required for interrogating previous metallic-based manufacturing, since such systems were developed based on several centuries of metal manufacturing experience. While x-ray technologies were adequate to perform subsurface measurements with metal substrates, concerns regarding health and safety of personnel have properly precluded their use and adaptation in all but the most carefully controlled environments, such as medical facilities.

SUMMARY

Aspects of this disclosure are directed to the use of second order and third order non-linear simultaneous mixing processes for the inspection and interrogation of surface materials in the THz spectral regime. The methods, systems and apparatuses disclosed allow the interrogation of both second order (e.g. sum frequency or difference frequency) and third order (e.g. stimulated Raman scattering or coherent anti-stokes Raman spectroscopy (CARS)) responses from a substrate material.

According to one aspect, the present disclosure is directed to a method for non-invasively evaluating a substrate material comprising directing a first optical input beam having a first frequency onto a predetermined area of a substrate material, substantially simultaneously directing a second optical input beam having a second frequency onto the predetermined area of the substrate surface, with the first frequency differing from the second frequency by a predetermined amount. The first optical input beam and the second optical input beam are mixed at the substrate surface to produce an output beam having a THz frequency, and receiving the output beam with a THz detector, wherein the first frequency of the first optical input beam differs from the second frequency of the second optical input beam. Because each of the interactions generated at the substrate material surface has different phase matching conditions, the signals will propagate away from the substrate material surface at different angles, allowing for spatial resolution of the differing surface signals. Stated another way, because the processes, systems and apparatuses according to the present disclosure are coherent, the direction of the output beams or signals from the substrate material will be different and distinct, allowing for their separation and the ability to measure the output signals independently.

According to one aspect, the present disclosure is directed to a non-linear method for non-invasively evaluating a substrate surface comprising the steps of providing a substrate material having a substrate material surface and a substrate material sub-surface, and providing a first optical source and a second optical source. A first input beam of radiation from the first optical source having a first frequency and a second input beam of radiation from the second optical source having a second frequency (the second input beam frequency different from the first input beam frequency by a predetermined amount) are substantially simultaneously directed to a predetermined area on the substrate material surface, and the first input beam and the second input beam are combined, or mixed, at the substrate material surface producing: 1) a second order output signal; and 2) a third order output signal in the THz regime. A second order output signal detector is positioned to receive second order output signals directed thereto from the substrate material surface. A third order output signal detector is positioned to receive third order output signals directed thereto from the substrate material surface. At least one characteristic of the substrate material is measured based on the second order output signals received by the second order output signal detector and the third order output signals received by the third order output signal detector.

According to a further aspect, in addition to the second and third order signals detectors, a first/second-harmonic signal detector is positioned to receive first/second-harmonic output signals from the substrate material surface, and a second/second-harmonic output signal detector is positioned to receive second/second-harmonic output signals from the substrate material surface. At least one characteristic of the substrate material is measured based on the first/second-harmonic output signals received by the first/second-harmonic output signal detector and the second/second-harmonic output signals received by the second/second-harmonic output signal detector.

According to another aspect, the first and second optical sources each comprise a frequency controller, an intensity controller and a bandwidth controller.

According to another aspect, the first and second optical input beams are combined at or near a predetermined area on the substrate material to create a surface difference frequency generation effect.

In a still further aspect, the first and second optical input beams are combined at or near a predetermined area on the substrate material to generate a CARS signal in the third order output signal.

According to another aspect, at least one of the first and second optical sources is a laser.

In another aspect, the first and second optical sources do not emit radiation in the THz wavelength range.

In yet another aspect, at least one optical source emits radiation to produce a second order signal and a third order signal, with the third order signal having a different surface phase-matching geometry relative to the second order signal.

In another aspect, the second order signal and the third order signal propagate from the predetermined area of the substrate material surface at differing angles.

According to a still further aspect, the first and second optical sources each emit radiation to the predetermined area on the substrate material surface at a differing predetermined frequency, with each optical source emitting radiation in the frequency range of from about 1 micron to about 0.2 micron.

In a further aspect, the sum of differing predetermined frequencies of radiation emitted from the first and second optical sources is substantially equal to the resonance of the substrate material at the substrate material surface.

According to a further aspect, one or more characteristics of the substrate material are measured based on the output signals received by detectors. The characteristics include but are not limited to the interrogation and evaluation of, for example, chemical composition and contamination, homogeneity, heterogeneity, mechanical surface irregularities (including, but not limited to, defects and contamination), material surface roughness, crystallographic defects, surface, etc., microstructural features, and combinations thereof.

According to still further aspects, the difference between the first frequency of the first optical input beam and the second frequency of the second optical input beam is a THz frequency in the range of from about 0.2 micron to about 1.0 micron.

According to further aspects of the present disclosure, the emitting device is not a THz wavelength emission source.

According to still further aspects, the first optical input beam and the second optical input beam are emitted from differing emitting devices, and the emitting devices may be lasers, with neither optical input beam being emitted from a THz wavelength emission source.

According to a further aspect, the output beam is non-co-linear with the first optical input beam and/or second optical input beam.

Still further, according to one aspect, the first optical input beam and the second optical input beam are directed onto a predetermined area of the substrate material simultaneously or substantially simultaneously.

A further aspect of the present disclosure contemplates a system for non-invasively evaluating a substrate surface. According to one aspect, a substrate having a substrate material surface and a substrate material sub-surface is provided. A first optical source and a second optical source are provided, with each optical source having a frequency controller, an intensity controller and a bandwidth controller. Each optical source is positioned to direct a beam of radiation substantially simultaneously to a predetermined area on the substrate material surface. The beams of radiation from the first and second optical sources are combined at or near the predetermined area of the substrate material. A second order signal detector is positioned to receive second order signals propagated from the substrate material. A third order detector is positioned to receive third order signals propagated from the substrate material. Characteristics of the predetermined area of the substrate material are measured based on the characteristics of the second order signals received by the second order detectors and the third order signals received by the third order detectors.

According to a further aspect, disclosed systems further comprise: 1) a first/second-harmonic output signal detector positioned to receive a first/second-harmonic output signal from a predetermined area on a substrate material and, 2) a second/second-harmonic output signal detector positioned to receive a second/second-harmonic output signal from a predetermined area on a substrate material.

According to a further aspect, the second order and third order signals are propagated from the substrate material surface at differing angles from one another.

In a still further aspect, the first/second-harmonic output signals and second/second-harmonic output signals propagate from the substrate material at differing angles relative to one another.

According to one embodiment, the optical sources are lasers, and the lasers do not emit radiation in the THz wavelength of from about 100 microns to about 1 mm.

In another aspect, the first and second optical input beams are combined at or near a predetermined area on the substrate material to create a surface difference frequency generation effect.

In a further aspect, the first and second optical input beams differ from one another by a frequency difference that is substantially equal to a resonance in the substrate material.

In a still further aspect, the first and second optical input beams are combined to generate a CARS signal in the third order output signal.

In another aspect, at least one optical source emits radiation to produce a second order effect signal and a third order effect signal, with the third order effect signal having a different surface phase-matching geometry relative to the second order effect signal.

In yet another aspect, the systems disclosed herein comprise or are otherwise in communication with computer software and/or hardware configured to measure one or more characteristics of the substrate material based on an output beam received by a detector.

According to further aspects of this disclosure, apparatuses are disclosed for non-invasively evaluating a substrate surface. According to one aspect, a substrate having a substrate material surface and a substrate material sub-surface is provided. Apparatuses comprise a first and second optical source, with each optical source having a frequency controller, an intensity controller and a bandwidth controller. Each optical source is positioned to direct a beam of radiation substantially simultaneously to a predetermined area on the substrate material surface. The beams from the optical sources are combined at the predetermined area of the substrate material surface. A second order signal detector is positioned to receive second order signals propagated from the substrate material. A third order detector is positioned to receive third order signals propagated from the substrate material. Features of the predetermined area of the substrate material surface are measured based on the characteristics of the second order and third order signals received by the second and third order detectors.

According to another aspect, the apparatuses further comprise: 1) a first/second-harmonic output signal detector positioned to receive a first/second-harmonic output signal from a predetermined area on a substrate material and, 2) a second/second-harmonic output signal detector positioned to receive a second/second-harmonic output signal from a predetermined area on a substrate material.

According to a still further aspect, the present disclosure is directed to a vehicle, including an aircraft, comprising a substrate material surface and a substrate material sub-surface, wherein at least a portion of the substrate material surface or substrate material sub-surface is interrogated by a non-linear method for non-invasively evaluating a substrate surface comprising the steps of providing a substrate material having a substrate material surface and a substrate material sub-surface, and providing a first optical source and a second optical source. A first input beam of radiation from the first optical source having a first frequency and a second input beam of radiation from the second optical source having a second frequency (the second input beam frequency different from the first input beam frequency by a predetermined amount) are substantially simultaneously directed to a predetermined area on the substrate material surface, and the first input beam and the second input beam are combined, or mixed, at the substrate material surface producing: 1) a second order output signal; and 2) a third order output signal in the THz regime. A second order output signal detector is positioned to receive second order output signals directed thereto from the substrate material surface. A third order output signal detector is positioned to receive third order output signals directed thereto from the substrate material surface. At least one characteristic of the substrate material is measured based on the second order output signals received by the second order output signal detector and the third order output signals received by the third order output signal detector.

For the purpose of this disclosure, the terms "area", "location" and "region" are used interchangeably and have equivalent meaning when referring to the substrate material.

For the purpose of this disclosure, the terms "interrogation" and "characterization" are used interchangeably and have equivalent meaning when referring to the substrate material.

For the purpose of this disclosure, the terms "characteristics" and "properties" are used interchangeably and have equivalent meaning when referring to the substrate material.

The methods, systems and apparatuses of the present disclosure provide solutions to the problems of accurately and cost-effectively interrogating and evaluating substrate material surface and sub-surface characteristics including, but not limited to the interrogation and evaluation of chemical composition, homogeneity, heterogeneity, mechanical surface irregularities (including, but not limited to, defects and contamination), crystallographic defects, surface, etc., and combinations thereof.

BRIEF DESCRIPTION OF THE DRAWINGS

Having thus described variations of the disclosure in general terms, reference will now be made to the accompanying drawings, which are not necessarily drawn to scale, and wherein:

DETAILED DESCRIPTION

According to one aspect, the present disclosure is directed to methods, systems and apparatuses for evaluating and characterizing substrate material surfaces and sub-surfaces in the THz regime by using a plurality of optical source input radiations (non-THz regime sources). According to another aspect, the optical sources undergo second order mixing, specifically difference frequency generation (DFG). The present methods, systems and apparatuses require only optical sources, but achieve the effect of using THz regime radiation. The optical sources of inherent interest exist in abundance, can be operated for long-duration with reduced maintenance, have a comparatively easy set-up, and can be easily inspected.

According to the methods, systems and apparatuses disclosed herein, it has now been demonstrated that THz regime investigation can be performed using only optical input sources that are in the optical regime. Desired effects in the THz regime are achieved via the use of non-linear optical interaction of optical source input beams at a material surface and/or sub-surface of a material being interrogated, by obtaining a difference frequency generation (DFG) between the two optical source inputs. According to the present disclosure, second order and third non-linear optical properties and processes are collected substantially simultaneously. More specifically, according to an aspect of the present disclosure, the difference frequency between a plurality of optical inputs (DFG), and the evaluation of the second harmonic of each of the optical inputs individually combined with the evaluation of third order effects are used to characterize a substrate material surface.

According to aspects of the present disclosure, Terahertz (THz) spectroscopy can be used for material evaluation and characterization by using second and third order non-linear mixing processes in the THz regime. According one aspect, the disclosed methods, systems and apparatuses provide optical configurations that interrogate a substrate material surface and subsurface by providing both second order (e.g. sum frequency or difference frequency) and third order (e.g. stimulated Raman scattering or coherent anti-stokes Raman spectroscopy) signals and responses. The combination of these technologies allows for higher speed (reduced evaluation time), higher amounts of data acquisition and higher accuracy, as well as additional correlation work between the signals.

According to aspects of the present disclosure, Terahertz (THz) spectroscopy can be used for material evaluation and characterization by using second and third order non-linear mixing processes in the THz regime. According one aspect, the disclosed methods, systems and apparatuses provide optical configurations that interrogate a substrate material surface and subsurface by providing both second order (e.g. sum frequency or difference frequency) and third order (e.g. stimulated Raman scattering or coherent anti-stokes Raman spectroscopy) signals and responses. The combination of these technologies allows for higher speed (reduced evaluation time), higher amounts of data acquisition and higher accuracy, as well as additional correlation work between the signals.

While the use of second order surface non-linear effects are known for surface diagnostics, combining these effects with coherent anti-stokes Raman spectroscopy (CARS) to achieve second and third order signals to achieve enhanced surface diagnostics is not known. Second order signals provide surface sensitivity. CARS provides a strong (third order) signal, as its signal involves gain within the material being interrogated. The combination of second order signals with CARS signals with cross correlation of the signals has now been determined to provide superior result in terms of non-invasive material interrogation. In addition, CARS signals can be generated with two inputs whose difference is equal to a resonance in the material being interrogated (e.g. a composite material). Surface difference frequency generation (DFG) can also be generated by the same two inputs. Third order effect (CARS) will provide different surface phase-matching geometries as compared to the second order effect. In this way, two output signals will propagate in different direction from the substrate material, making it possible and easier to separate the spectral signals. Analytically, the signals can be compared to one another, over-constraining the equations associated with their generation, so that precise values for the coefficients associated with the material being interrogated can be deduced from the signals. In addition, each of the input signals will independently produce a second harmonic signal coincident with the spectral reflection from the material being interrogated. This provides additional analytical constraint to the numerical responses produced.

The required frequencies are obtained by providing difference frequency generation (DFG) at a material surface interface. It has now been determined that, so long as the difference between the input frequencies from the input sources are in the THz regime, a useful THz output will be generated at the material surface, and the THz output signal can be interrogated with an appropriately positioned THz sensor.

According to a further aspect, optical (laser) inputs may be used to achieve the desired input frequencies, and the inputs are tuned to differ in frequency by the THz frequency. In an alternate aspect, an individual laser contains multiple frequency components to achieve a THz frequency.

According to aspects of the disclosure, since there is a substantial shift in frequencies between the input and output frequencies, the background signal is greatly reduced, producing higher signal to noise ratio and overcoming problems previously associated in the field.

The source responsible for the DFG is the nonlinear polarization $P^{(2)}$ in the medium.

$$\vec{P}^{(2)}(\omega_{THz}=\omega_1-\omega_2)=\vec{\chi}^{(2)}(\omega_{THz}):\vec{E}(\omega_1)\vec{E}(\omega_2).$$

If the medium has an inversion symmetry, then the nonlinear susceptibility $\vec{\chi}^{(2)}$ vanishes in the electric-dipole approximation. Since the inversion symmetry is necessarily broken at an interface, this makes DFG an effective surface probe. For a monolayer of molecules at a surface, the surface nonlinear susceptibility is typically ~10-15 esu, which should yield a signal of $10^3$ photons/pulse with a laser pulse of 10 milliJoule energy and 10 nsec duration impinging on a surface area of $0.2$ cm$^2$.

The resonant behavior of $\vec{\chi}^{(2)}$ can provide spectroscopic information about a surface or molecules adsorbed at the surface. However, if optical wavelengths are involved in the inputs, which are generally in the 0.2 to 1 micron range, only electronic transitions of the molecules or surface structure can be probed. Such wavelengths usually have relatively broad bandwidths, making DFG not particularly useful for identification or selective monitoring of surface molecular species. Vibrational spectroscopy is more suitable for selective studies of adsorbed molecules and their interaction with the substrate. Vibrational modes appear in the IR or THz range, and sources in the THz range suitable for nonlinear optics, do not exist.

In the DFG process, the difference in frequency between the two non-THz input beams is tuned through a vibrational resonance, and the THz signal is generated directly at the surface. When the difference frequency is resonant with a material resonance at the surface, x has a resonant enhancement (i.e., it gets larger) so the THz response can be measured even though the inputs are in the optical regime.

Figure 1:
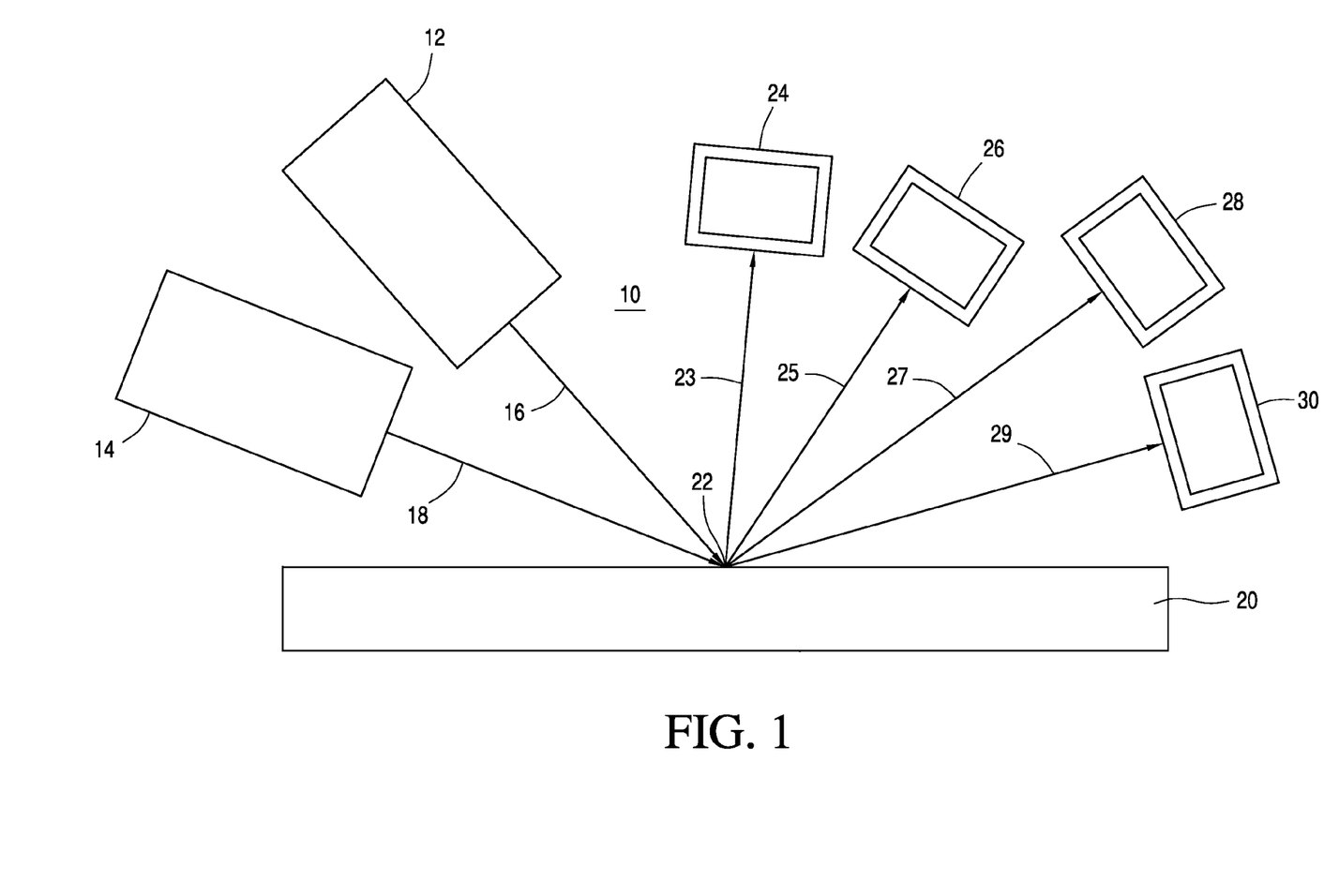
FIG. 1 is schematic diagram of one aspect of the present disclosure.
Figure 2:
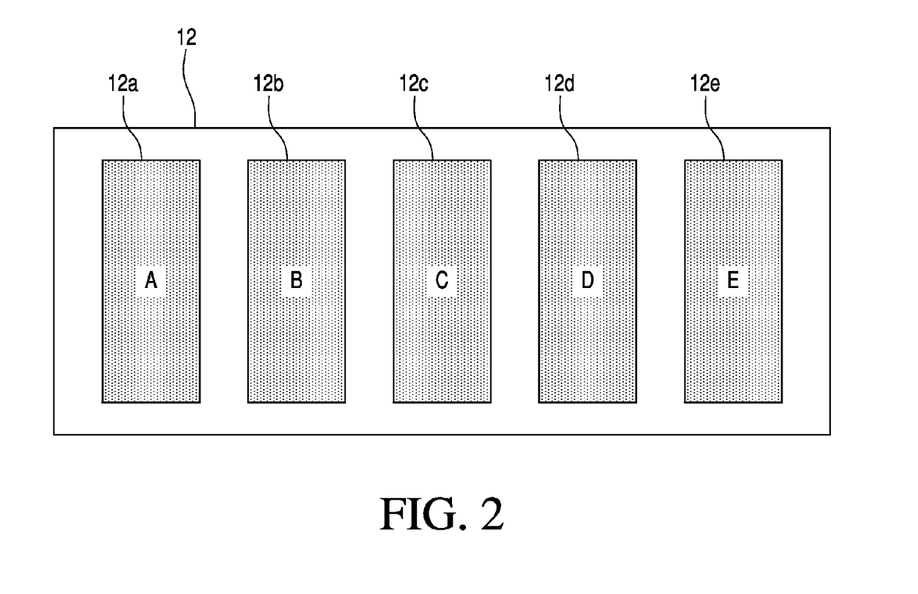
FIG. 2 is schematic diagram of one aspect of the present disclosure.
Figure 3:
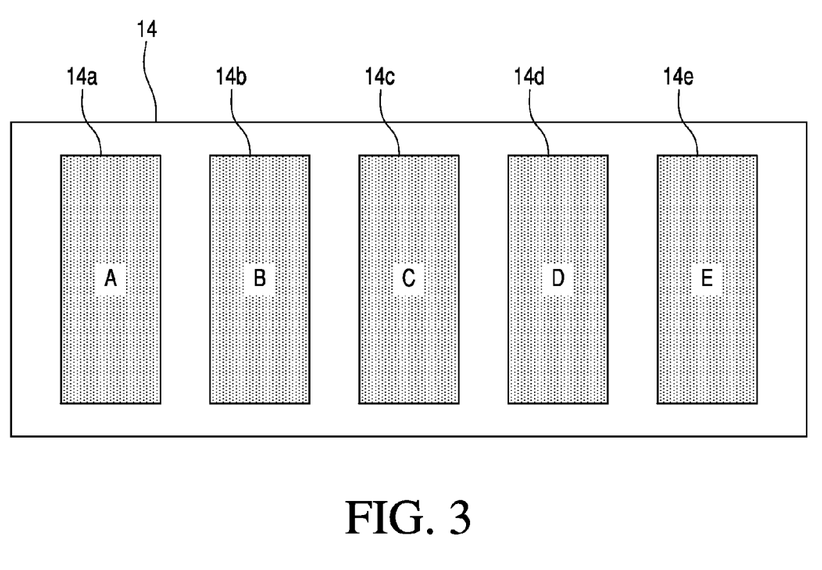
FIG. 3 is schematic diagram of one aspect of the present disclosure.

FIGS. 1-3 show schematic representation of aspects of the present disclosure. As shown in FIG. 1, diagnostic system 10 shows a first optical source 12 and a second optical source 14. As shown in greater detail in FIG. 2, first optical source 12 comprises: an optical source of electromagnetic radiation in the optical regime 12a; optical elements for regulation and control of radiation intensity 12b; optical elements for control of radiation polarization 12c; optical elements for control of radiation bandwidth 12d; and optical elements for control of the manner of radiation propagation, such as, for example, lenses 12e. It is understood that the elements 12a-12e are illustrative and that the order and location in which they are positioned within optical source 12 is not meant to be restrictive in any way. As shown in greater detail in FIG. 3, second optical source 14 comprises: a source of electromagnetic radiation in the optical regime 14a; elements for regulation and control of radiation intensity 14b; elements for control of radiation polarization 14c; elements for control of radiation bandwidth 14d; and elements for control of the manner of radiation propagation, such as, for example, lenses 14e. In one aspect, the frequency and bandwidth controls on the first and second optical sources must be such that their frequency separation is equal to a frequency in the THz frequency band of interest, and the bandwidth of each optical source must be narrower than the separation (for example, according to one aspect, the bandwidth must be about 1/10 of the separation). As shown in FIG. 1, first optical source 12 emits a tunable non-terahertz range first input beam 16 that is directable onto a predetermined area 22 on a surface 20 being interrogated. According to one aspect, wavelengths of the first and second optical can usefully be, but are not necessarily, in the range of from about 0.2 micron to about 1 micron. Second optical source 14 emits a tunable non-terahertz range second input beam 18 that is directable onto a predetermined area 22 on a surface 20 being interrogated. The first and second optical sources are aligned in a predetermined orientation so that their surface areas of optical illumination overlap on the interrogated surface 20 and are combined. This alignment may be implemented via a series of refractive and reflective elements. For example, by changing their tilt in two axes, elements in series can propagate a laser beam to any position on a surface.

Second order signal detector 24 receives a second order output signal 23 from the predetermined area 22 on a substrate material surface 20 being interrogated. Third order signal detector 26 receives a third order output signal 25 from the predetermined area 22 on a substrate material surface 20 being interrogated. In addition, a first/second-harmonic output detector 28 is positioned to receive a first/second-harmonic output 27 from the predetermined area 22 on a substrate material surface 20 being interrogated. A second/second-harmonic output detector 30 is positioned to receive a second/second-harmonic output 29 from the predetermined area 22 on a substrate material surface 20 being interrogated.

The first and second optical sources 12, 14 include a visible input in optical communication with associated input optics. The first and second optical sources 12, 14 preferably comprise a narrow frequency bandwidth visible pulse laser, such as, for example, a pulsed diode laser, a continuous wave diode laser, a pulsed solid state laser, or a continuous wave solid state laser, etc.

According to one aspect, the optical source may comprise a Nd:YAG laser operating on the 1.064 micron line, or a Nd:YAG laser and a harmonic converter for operation at the second or third harmonic of the fundamental output wavelength. It may operate with a maximum pulse length of about 10 nsec, with the optimal pulse length being about 10 psec. According to further aspects, the optical sources comprise tunable visible input capabilities including steering apparatuses that may comprise mirrors aligned so that their surface normal are non-coplanar, with the mirrors' reflectances being optimized for an output wavelength of the tunable visible laser. Polarizers may be used that are operative in the visible range so that an output wavelength is p or s polarized with the polarization referenced to the surface to be interrogated. In one aspect, a spot shaping apparatus is used that may include a series of lenses for creating a predetermined and controlled spot size on the surface to be interrogated. The lenses may be transparent in the visible range.

The output wavelength discriminator preferably includes an iris, a filter in communication with the iris for passing output sum frequency wavelength, and a polarizer in optical communication with the filter aligned to detect either the p or s polarization and referenced to the surface where the sum frequency output signal is generated.

According to another aspect of the disclosure, the signal collection optics may include a telescope system comprising a plurality of lenses having desired materials and coatings optimized for the sum frequency output wavelength, in the wavelength band from about 0.2 micron to about 1.0 micron. The optical detector may be based on a semiconductor material such as, for example, silicon, germanium, etc. depending upon the precise wavelength to be detected. The detector may be electronically gated to only detect output light generated by the input laser pulses. A computer collects and analyses the electronic data from the optical detector.

The frequency structure of the laser pulse may comprise several frequencies, with the lines defined by the longitudinal modes of the laser. As an alternative to narrowing the bandwidth, the longitudinal modes of each input can be spaced so that the difference frequency between the modes will form the THz frequency difference. This will allow for the DFG process to occur, even if the overall bandwidths of the laser pulses are broad. According to another variation, a single laser may be used having individual longitudinal lines to form the DFG inputs. A THz signal is then be created by the DFG between those individual lines. In this way, the absolute frequency of the first optical source is not critical, so long as the relative separation between the two optical sources is predictably controlled and maintained. Optical frequency and bandwidth controls may include optical filters, diffraction gratings, Fabry-Perot etalons, etc., any of which can be used internally to the optical sources (i.e. laser cavity) or externally from the optical sources.

Figure 4:
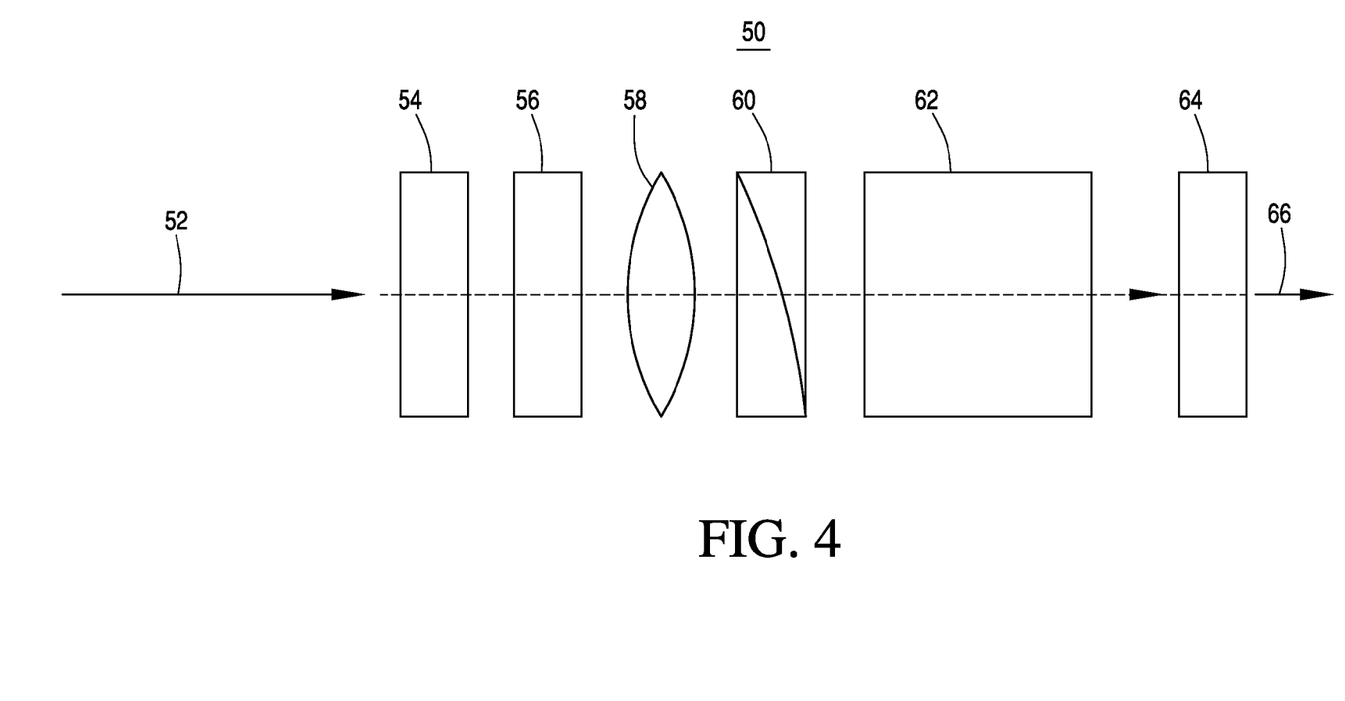
FIG. 4 is schematic diagram of one aspect of the present disclosure.

According to another aspect of the present disclosure, the detector 24 will be responsive or sensitive to THz signals at the THz frequency band and comprise, at least, a frequency (wavelength) THz discriminator, an intensity control, and a polarization discriminator. Detectors 26, 28 and 30 may comprise components necessary to receive and process the signals generated by the combined first and second inputs that are propagated to the detectors from a substrate material being interrogated, and be responsive or sensitive to signals that are in the optical range. FIG. 4 shows a schematic diagram of exemplary components that may be present in the detectors 24, 26, 28, 30, according to one variation. According to system array 50 shown in FIG. 4, the DFG signal 52 is directed to and received by a direction selector 54, such as, for example, an iris. DFG signal 52 then proceed through direction selection 54 and through the following components in sequence: broadband frequency selector 56; collection device, such as, for example, a lens or lens combination 58; a polarization selector 60 to accept p or s as needed; a spectrophotometer 62; and electrical signal converter 64, such as, for example, a photodiode or equivalent component for use to convert a signal in the visible spectrum. A converted electrical signal 66 then passes from the system array 50 to processing architecture (not shown) in communication with desired computer hardware and software that is able to recognize, interpret, classify and otherwise assist in the interrogation of the substrate material.

According to further aspects of the disclosure, detection apparatuses will comprise frequency-selective elements to allow discrimination between the difference frequency signal and other ambient or interfering signals that may be generated in the area of measurement at or beneath the substrate material surface. The signal collection optics receive the propagation of the output from the first and second optical sources so that a collected optical light signal is formed after propagation through the signal collection optics. The signal collection optics may be either refractive or reflective optics that act to control the divergence of the light coming from the surface being interrogated so that as much of the light signal as possible is collected for analysis. According to a further variation, an optical detector converts the collected optical light signal to an electronic signal, thus monitoring the intensity of the DFG as a function of surface characterization. An electronic signal analyzer analyzes the electron signal for providing surface-sensitive spectroscopic characterizations. According to one aspect, the electronic signal analyzer may be, for example, a computer with suitable internal electronics to implement the appropriate mathematical algorithms to interpret the received electronic signals. According to one aspect, the presence of contamination on a surface being interrogated will change the spectroscopic response of the surface. Since the amount of light generated at the DFG wavelength will depend upon the surface spectroscopy, appropriate interpretation of the electronic signal provides a means to monitor the amount of contamination present on the surface.

According to one aspect, because the optical sources of the present disclosure require diagnostics requiring a non-linear optical source interaction, pulse lasers with desired peak intensities of from about 1 KW/cm$^2$ to about 1 GW/cm$^2$ are contemplated. One contemplated laser source are solid-state lasers, such as, for example, Nd:YAG lasers operating on the 1.064 micron line, or a Nd:YAG laser and a harmonic converter for operation at the second or third harmonic of the fundamental output wavelength. Such a source may operate with a maximum pulse length of about 10 nsec, with the optimal pulse length being about 10 psec. The useful range for the difference frequency is the THz spectrum of from about 0.1 THz to about 100 THz. More complex lasers such as Ti:sapphire lasers are also contemplated. The contemplated lasers are commercially available from sources including Coherent, Spectra-Physics, Melles-Griot, etc.

According to further aspects, the optical sources comprise tunable visible input capabilities including steering apparatuses that may comprise mirrors aligned so that their surface normal are non-coplanar, with the mirrors' reflectances being optimized for an output wavelength of the tunable visible laser. Polarizers may be used that are operative in the visible range so that an output wavelength is p or s polarized with the polarization referenced to the surface to be interrogated. In one aspect, a spot shaping apparatus is used that may include a series of lenses for creating a predetermined and controlled spot size on the surface to be interrogated. The lenses may be transparent in the visible range.

The output wavelength discriminator preferably includes an iris, a filter in communication with the iris for passing the DFG wavelength, and a polarizer in optical communication with the filter aligned to detect either the p or s polarization and referenced to the surface where the DFG light is generated.

According to another aspect of the disclosure, the signal collection optics may include a telescope system comprising a plurality of lenses having desired materials and coatings optimized for the DFG wavelength, in the wavelength band from about 0.3 mm to about 30 microns. The optical detector may be based on a semiconductor material such as, for example, silicon, germanium, etc. depending upon the precise wavelength to be detected. The detector may be electronically gated to only detect output light generated by the input laser pulses. A computer collects and analyses the electronic data from the optical detector.

According to one contemplated variation, within the THz detectors 24, 26, 28, 30, signal collection optics receive the combined output from the first and second optical sources that is reflected from the surface being interrogated. The signal collection optics direct the propagation of the output from the first and second optical sources so that a collected optical light signal is formed after propagation through the signal collection optics. The signal collection optics may be either refractive or reflective optics that act to control the divergence of the light coming from the surface being interrogated so that as much of the light signal as possible is collected for analysis. According to a further variation, an optical detector converts the collected optical light signal to an electronic signal, thus monitoring the intensity of the DFG as a function of surface characterization. An electronic signal analyzer analyzes the electron signal for providing surface-sensitive spectroscopic characterizations. According to one aspect, the electronic signal analyzer may be, for example, a computer with suitable internal electronics to implement the appropriate mathematical algorithms to interpret the received electronic signals.

According to one aspect, the presence of contamination on a surface being interrogated will change the spectroscopic response of the surface. Since the amount of light generated at the DFG wavelength will depend upon the surface spectroscopy, appropriate interpretation of the electronic signal provides a means to monitor the amount of contamination present on the surface.

According to one aspect, the optical sources may comprise a Nd:YAG laser operating on the 1.064 micron line, or a Nd:YAG laser and a harmonic converter for operation at the second or third harmonic of the fundamental output wavelength. It may operate with a maximum pulse length of about 10 nsec, with the optimal pulse length being about 10 psec. In another aspect, the first input beam and the second input beam are directed onto a predetermined area of the substrate material simultaneously or substantially simultaneously.

Since it is understood that pulsed lasers have a temporal duration of, typically about, one nanosecond or one picosecond, according to aspects of this disclosure, "substantially simultaneously" refers to laser pulses arriving at a predetermined area or region on a substrate material surface, such that their pulses arrive at the substrate material surface in overlapping fashion, and the pulses are out of synch for only a duration of from about 50 to about 100 picoseconds.

According to further aspects, the optical sources comprise tunable visible input capabilities including steering apparatuses that may comprise mirrors aligned so that their surface normal are non-coplanar, with the mirrors' reflectances being optimized for an output wavelength of the tunable visible laser. Polarizers may be used that are operative in the visible range so that an output wavelength is p or s polarized with the polarization referenced to the surface to be interrogated. In one aspect, a spot shaping apparatus is used that may include a series of lenses for creating a predetermined and controlled spot size on the surface to be interrogated. The lenses may be transparent in the visible range.

The output wavelength discriminator preferably includes an iris, a filter in communication with the iris for passing the DFG wavelength, and a polarizer in optical communication with the filter aligned to detect either the p or s polarization and referenced to the surface where the DFG light is generated.

According to another aspect of the disclosure, the signal collection optics may include a telescope system comprising a plurality of lenses having desired materials and coatings optimized for the DFG wavelength, in the wavelength band from about 1000 microns to about 100 microns. The optical detector may be based on a semiconductor material such as, for example, silicon, germanium, etc. depending upon the precise wavelength to be detected. The detector may be electronically gated to only detect output light generated by the input laser pulses. A computer collects and analyses the electronic data from the optical detector.

According to one contemplated variation, within the detector 30, signal collection optics receive the combined output from the first and second optical sources that is reflected from the surface being interrogated. The signal collection optics direct the propagation of the THz second harmonic frequency output so that a THz frequency output signal is formed after propagation through the signal collection optics. The signal collection optics may be either refractive or reflective optics that act to control the divergence of the light coming from the surface being interrogated so that as much of the THz light signal as possible is collected for analysis. According to a further variation, an optical detector converts the collected optical light signal to an electronic signal, thus monitoring the intensity of the THz second harmonic frequency output signal as a function of surface characterization. An electronic signal analyzer analyzes the electron signal for providing surface-sensitive spectroscopic characterizations.

According to one aspect, as would be readily understood by one skilled in the field, an electronic signal analyzer may comprise, for example, a computer with suitable internal electronics, including appropriate hardware and software to implement the appropriate mathematical algorithms to interpret the received electronic signals. The electronic signal analyzer may be located within the detector, may be in communication with the detector, and may be located remotely from the detector but in communication with the detector via known wireless or wired means as would be understood by one skilled in the field.

According to one contemplated variation, actual test setup hardware is analogous to systems used for sum frequency generation spectroscopy in the infrared or visible regions. The optical inputs are laser sources typically solid-state lasers (for example, Nd:YAG) as such laser types have high peak powers that are optimal for use in non-linear surface mixing systems. The sources separately will pass through an optical filter to remove any straight light that may be present at the anticipated and preselected frequencies, thus insuring that the signals detected by the detectors are actually generated at the substrate material surface and are not occurring due to some residual signal present in the inputs. After filtering, the light passes through a telescoping lens system designed to reduce the spot size to an optimum diameter or area for generating surface signal. This may vary somewhat although values in the 1 mm range are appropriate. Although it is not essential for surface diagnostics, a separate polarization control system for the light may also be present. Polarization control systems may consist of a polarizer and other polarization elements such as a quarter wave plate or half wave plate. Specific operational protocols may involve synchronizing laser pulses in time and space on the substrate material. For example, two pulses may be synchronized in time, typically by monitoring their time profile with some external diagnostic, to make certain that they arrive at the surface simultaneously or substantially simultaneously. In addition, two pulses are aligned so that they physically overlap at a predetermined area on a substrate material surface. Care must be taken to achieve such overlap, as the sources originate from different physical locations. The output signals are not directly visible, but since they are coherent, the direction of propagation from the substrate material relative to the reflected inputs can be calculated. Simple geometry can then be used to locate the signal position relative to the reflected signals. The signal light will then be collected by a lens or telescope system, and passed through optical filters to remove any stray input light that may be coincident with the output direction. The signal will also then be passed through frequency selective elements, such as, for example, a spectrophotometer, and detected with an appropriate detection system such as, for example, a photo diode or photomultiplier.

Although the aspects of the present disclosure are useful for all materials regardless of the materials' end uses, material and material surfaces and sub-surfaces interrogated by the methods, systems and apparatuses of the present disclosure are thought to be particularly useful interrogating materials used a components and parts in the manufacture of, for example, manned or unmanned objects and structures in an atmospheric or space environment. Contemplated objects include structures and vehicles, such as, for example, aircraft, satellites, rockets, missiles, etc., and therefor include manned and unmanned aircraft, spacecraft, terrestrial vehicles, non-terrestrial vehicles and even surface and sub-surface waterborne marine vehicles, objects and structures.

Figure 5:
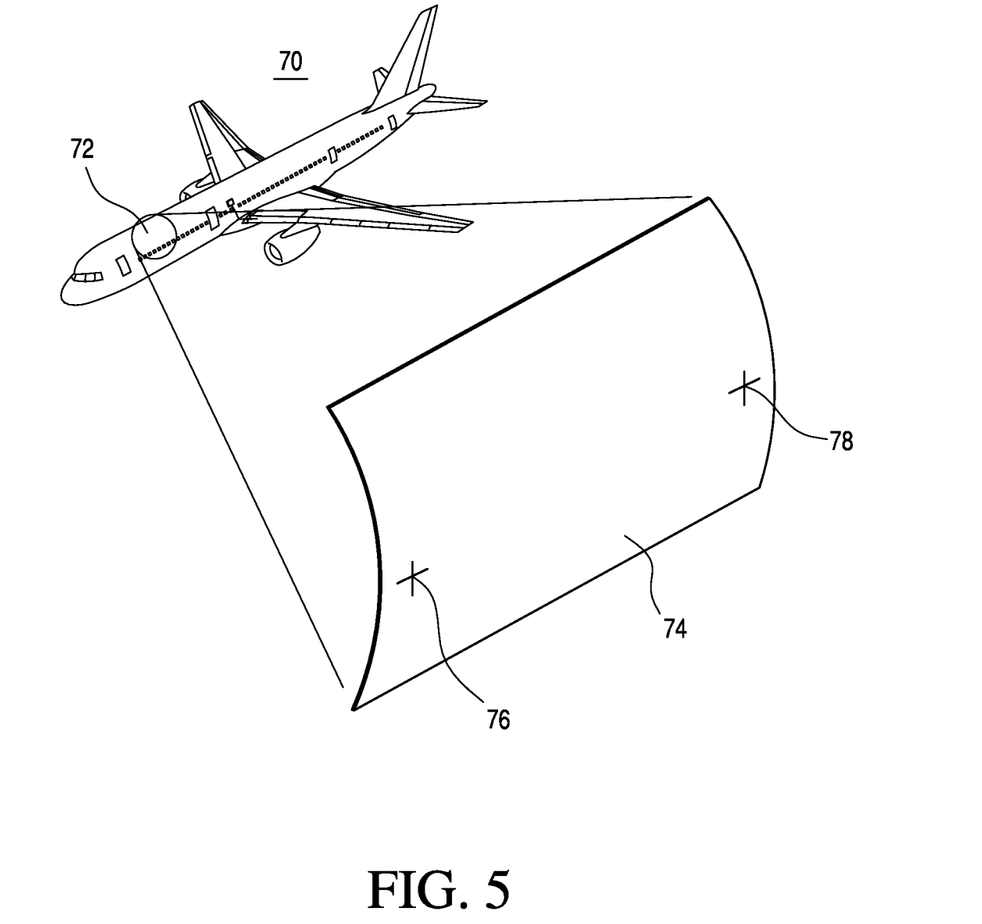
FIG. 5 is a drawing of an aircraft comprising material interrogated by an aspect of the present disclosure.

FIG. 5 is a drawing of a vehicle, and, in particular, an aircraft 70. Fuselage panel 74 having a substrate material surface is shown, in an enlarged configuration, as being located at the region of the fuselage at location 72. The marks shown as "+" 76, 78 represent locations on the substrate material surface of fuselage panel 74 that may be interrogated according to methods, systems and apparatuses of the present disclosure. While the drawing shows an aircraft with a portion of fuselage identified, it is understood that the methods, systems and apparatuses of the present disclosure contemplate use with any material substrate surface of any material that can be used anywhere in the construction of any vehicle, such as, for example an aircraft, including the interior, exterior or locations there between.

While the preferred variations and alternatives of the present disclosure have been illustrated and described, it will be appreciated that various changes and substitutions can be made therein without departing from the spirit and scope of the disclosure. Accordingly, the scope of the disclosure should only be limited by the accompanying claims and equivalents thereof.

We claim:

1. A method for non-invasively evaluating a substrate material comprising the steps of:
   substantially simultaneously directing a first input beam of radiation having a first frequency from a first optical source and a second input beam of radiation having a second frequency from a second optical source to a predetermined area on a substrate material surface, with the first frequency differing from the second frequency by a predetermined amount;
   mixing the first input beam and the second input beam at the substrate material surface;
   producing second order and third order output signals in the THz regime from the substrate material;
   directing the second order output signal to a second order output signal detector to receive the second order output signal from the substrate material;

directing the third order output signal to a third order output signal detector to receive the third order output signal from the substrate material; and measuring at least one characteristic of the substrate material based on the second output signal and third output signal received by the second order output signal detector and the third order output signal detector.

2. The method of claim 1 further comprising the steps of:

directing a first/second-harmonic output signal to a first/second output signal detector positioned to receive a first/second-harmonic output signal from the first optical source;

directing a second/second-harmonic output signal to a second/second-harmonic output detector positioned to receive a second/second-harmonic output signal from the second optical source; and measuring at least one characteristic of the substrate material based on the first/second-harmonic output signal received by the first/second-harmonic output signal detector and the second/second-harmonic output signal received by the second/second-harmonic output signal detector.

3. The method of claim 2, wherein the first and second optical sources each comprise:
a frequency controller;
an intensity controller; and
a bandwidth controller.

4. The method of claim 1, wherein the first and second optical sources each comprise:
a frequency controller;
an intensity controller; and
a bandwidth controller.

5. The method of claim 1, wherein the first and second optical input beams are combined to create a surface difference frequency generation effect.

6. The method of claim 1, wherein the first and second input beams differ from one another by a frequency difference that is substantially equal to a resonance in the substrate surface material.

7. The method of claim 1, wherein the first and second optical input beams are combined to generate a CARS signal in the third order output signal.

8. The method of claim 1, wherein at least one of the first and second optical sources is a laser.

9. The method of claim 1, wherein the optical sources do not emit radiation in the THz range.

10. The method of claim 1, wherein at least one optical source emits radiation to produce a second order signal and a third order signal, with the third order signal having a different surface phase-matching geometry relative to the second order signal.

11. The method of claim 10, wherein the second order signal and the third order signal propagate from the predetermined area of the substrate material surface at differing angles.

12. A system for non-invasively evaluating a substrate material comprising:

a substrate having a substrate material surface and a substrate material sub-surface;

a plurality of optical sources, each optical source comprising a frequency controller, and intensity controller and a bandwidth controller, with each optical source positioned to direct a beam of radiation substantially simultaneously to a predetermined area on the substrate material surface, and wherein the beam of radiation from a first optical source and a second optical source are combined at the predetermined area on the substrate material surface;

a second order signal detector positioned to receive second order signals from the predetermined area of the substrate material; and a third order detector, said third order detector positioned to receive third order signals from the predetermined area of the substrate material;

wherein characteristics of the predetermined area of the substrate material are measured based on the characteristics of the output signals received by the second order detector and the third order detector.

13. The system of claim 12, further comprising:

a first/second-harmonic detector positioned to receive a first/second-harmonic output signal from the predetermined area of the substrate material surface, and a second/second-harmonic detector positioned to receive a second/second-harmonic output signal from the predetermined area of the substrate material.

14. The system of claim 13, further comprising computer software and/or hardware configured to measure one or more properties of the substrate material based on an output beam received by a detector.

15. The system of claim 12, wherein the second order signals and third order signals are propagated from the predetermined area of the substrate material at differing angles.

16. The system of claim 13, wherein the first/second-harmonic output signals and the second/second-harmonic output signals propagate from the predetermined area of the substrate material at differing angles.

17. The system of claim 12, wherein the optical sources do not emit radiation in the Terahertz wavelength range.

18. The system of claim 12, wherein the first optical input beams and second optical input beams are combined at the predetermined area of the substrate material to create a surface difference frequency generation effect.

19. The system of claim 12, wherein the first optical input beams and the second optical input beams differ from one another by a frequency difference that is substantially equal to a resonance in the substrate material.

20. The system of claim 12, wherein the first and second optical input beams are combined to generate a CARS signal in the third order output signal.

21. The system of claim 12, wherein at least one optical source emits radiation to produce a second order effect signal and a third order effect signal, with the third order effect signal having a different surface phase-matching geometry relative to the second order effect signal.

22. The system of claim 12, further comprising computer software and/or hardware configured to measure one or more characteristics of the substrate material based on an output beam received by a detector.

23. A vehicle comprising a substrate material surface and a substrate material sub-surface, wherein at least a portion of the substrate material surface or substrate material sub-surface is interrogated by:

substantially simultaneously directing a first input beam of radiation having a first frequency from the first optical source and a second input beam of radiation having a second frequency from the second optical source to a predetermined area on a substrate material surface, with the first frequency differing from the second frequency by a predetermined amount;

mixing the first input beam and the second input beam at the substrate material surface;

producing second order and third order output signals in the THz regime from the substrate material;

directing the second order output signal to a second order output signal detector to receive the second order output signal from the substrate material;

directing the third order output signal to a third order output signal detector to receive the third order output signal from the substrate material; and measuring at least one property of the substrate material based on the second output signal and third output signal received by the second order output signal detector and the third order output signal detector.

24. A vehicle according to claim 23, wherein the vehicle is an aircraft.

\* \* \* \* \*